United States Patent [19]
Chateau

[11] Patent Number: 5,746,975
[45] Date of Patent: May 5, 1998

[54] APPARATUS FOR IMMUNOLOGICAL ANALYSIS

[75] Inventor: Sophie Chateau, Camon, France

[73] Assignee: SCIBIEX (SARL), France

[21] Appl. No.: 782,526

[22] Filed: Jan. 10, 1997

Related U.S. Application Data

[63] Continuation of Ser. No. 424,701, Apr. 18, 1995, abandoned.

[30] Foreign Application Priority Data

Apr. 22, 1994 [FR] France .................. 94 05123

[51] Int. Cl.$^6$ ................................. G01N 21/07
[52] U.S. Cl. ................... 422/61; 422/72; 422/102
[58] Field of Search ................. 422/61, 72, 102; 436/808, 809

[56] References Cited

U.S. PATENT DOCUMENTS

| | | | |
|---|---|---|---|
| 3,825,410 | 7/1974 | Bagshawe | 422/102 |
| 4,252,538 | 2/1981 | Barr | 422/61 |
| 5,149,501 | 9/1992 | Babson et al. | 422/61 |

FOREIGN PATENT DOCUMENTS

| | | | |
|---|---|---|---|
| 0054087 | 6/1982 | European Pat. Off. | |
| 0104881 | 4/1984 | European Pat. Off. | |
| 9108491 | 6/1991 | WIPO | G01N 35/04 |
| 9303374 | 2/1993 | WIPO | |

*Primary Examiner*—Lyle A. Alexander
*Attorney, Agent, or Firm*—Ladas & Parry

[57] ABSTRACT

The apparatus of the invention is in the form of a kit comprising two distinct elements designed to be assembled together and to co-operate during immunological analysis. The first element is an incubation element that includes at least one receptacle suitable for receiving a mixture comprising a substance to be analyzed and a test substance. The second element is a reaction element and includes at least one well which is closed by a sealing membrane and which has a bottom on which a reactionally sensitive layer is fixed. The apparatus includes means for assembling said elements together and perforation and injection means, e.g. a tapering tube, projecting from the bottom of the receptacle of the incubation element and extending outwards, said means being suitable firstly for perforating the membrane and then for injecting the contents of the receptacle into the well through said perforated membrane, once the two elements have been assembled together. The method consists in assembling the two elements together so that the tapering tube perforates the membrane and penetrates into the well, in incubating them, and then in centrifuging them at a speed sufficient to cause the mixture to pass from the receptacle into the well via the tapering tube.

9 Claims, 2 Drawing Sheets

APPARATUS FOR IMMUNOLOGICAL ANALYSIS

This is a continuation of application(s) Ser. No. 0/08/424,701 filed on Apr. 18, 1995, now abandoned.

FIELD OF THE INVENTION

The present invention relates to improved apparatus for immunological analysis, and in particular for immunohematological analysis, implementing a solid phase reaction chamber. More particularly, the invention relates to apparatus in the form of a kit comprising two distinct elements, one constituting the incubation element and the other the reaction element. The present invention also relates to a method specially designed for implementing the above-specified apparatus.

BACKGROUND OF THE INVENTION

Antibody screening techniques as used in the context of blood transfusions, have recently developed considerably compared with conventional techniques implemented in test tubes or on plates.

A so-called "solid phase" first technique consists in fixing test red blood cells in stable manner at the bottoms of U-shaped wells made of plastics material. The wells are associated to form a microtiter plate comprising 96 wells, or else they form strips that comprise 8 or 12 wells.

In the technique proposed by the firm Immucor, serum from a patient is screened for antibodies that are directed specifically against certain antigens present on the immobilized test red blood cells, i.e. the red blood cells fixed to the plastics material constituting the bottom of each well. The screening is performed by a first step during which the serum is incubated in the well that has been sensitized in this way, followed by a washing operation (which is generally repeated five times), thereby eliminating any non-fixed antibodies, and finally by adding a suspension of an indicator constituted by red blood cells coated with human antiglobulins. By centrifuging, the indicator comes into contact with the bottom of the well; if the antibodies present in the serum have been retained by the test red blood cells immobilized on said bottom, then the indicator is caused to adhere thereto, thereby giving rise to a uniform image over the entire bottom of the well. The image is interpreted as a positive reaction. In contrast, if no antibody is fixed, then the indicator does not adhere to the red blood cells secured over the entire bottom of the well and so it gathers together in the middle thereof, thus giving rise to an image of central button. This image is interpreted as being a negative reaction.

In the Immucor technique, microtiter plates are delivered in the dried state. Either the bottoms of the wells are sensitized with dyes and the user has to prepare the sensitive layer of test red blood cells, or else the sensitive layer of red blood cells is prepared in advance and delivered in freeze-dried form.

In a variant of that solid phase technique, as proposed by the firm Biotest, the bottom of the well is covered in globulin, with the microtiter plates or strips being delivered in dried form.

Under such circumstances, the user incubates a mixture in the wells, which mixture is made up of serum from the patient and test red blood cells that are delivered in suspension. After incubation, the user must wash the red blood cells in situ so as to eliminate free proteins from the mixture. Thereafter, the user adds a liquid antiglobulin and applies centrifuging to cause the red blood cells, the antibodies, and the antiglobulins to react with the bottom of the well which is covered in globulins.

The Immucor technique takes account only of IgG type antibodies whereas, in theory, the Biotest technique is capable of showing up all classes of immunoglobulin. However, the Biotest technique is considered as being difficult to implement.

In both cases, the need to dry substances which are fixed on the bottoms of the wells that are made of plastics material constitutes a major constraint on the manufacture of microtiter plates or strips. In addition, drying or freeze-drying requires the addition of protective substances which are nevertheless certain at least to some extent to spoil the biological activities of the substances that have been fixed.

A second technique is known under the initials TAC, i.e. "Techniques d'Agglutinations en Colonnes" [Column clumping techniques]. It is proposed by the firms Diamed, and Ortho. Such column techniques make use of microtubes that are associated with one another to form cards or cassettes that generally include six columns, each being constituted by a tube that contains either Sephadex gel, or the like, or microbeads of glass in suspension in a special diluant. The top of each column flares to form an incubation chamber suitable for receiving red blood cells and serums to be screened for antibodies. The gel or the diluant contains Coombs' serum based on human antiglobulins or else an inert diluant in techniques that use proteolytic enzymes. For blood grouping, the gel or the special diluant contain test serums, and grouping is performed in exactly the same way as antibody screening.

In general, this TAC second technique has turned out to be more sensitive than conventional test tube techniques and more convenient than solid phase techniques; in particular, for antiglobulin reactions, it avoids any need for the user to perform the washing stages that are required for eliminating non-fixed proteins.

The gel or the diluant, when associated with glass microbeads, performs the role of a density gradient, allowing red blood cells to pass but not free proteins. The gel or the microbeads have the ability of retaining agglutinates at the top of the column while passing non-agglutinated red blood cells under the influence of centrifugal force. The agglutinates are created either in the incubation chamber or else on contact with the reagents contained in the gel or in the diluant.

Unlike the first technique which is a solid phase technique, the reagents contained in the columns are in the liquid state. A plastic-coated metal foil binded to the top of the cassette serves to seal it; it must be removed immediately prior to use. The TAC technique nevertheless suffers from certain drawbacks. The columns of gel or of microbeads are easily damaged during transport, since they are particularly sensitive to shock. In addition, when the cassettes are opened by removing the protective foil, splashes are often observed, and they destroy or at least spoil the quality of the results, and they can be responsible for cross-contamination. During transport, drops of reagent can be splashed onto the foil and can then contaminate the other columns when the foil is removed.

Furthermore, condensation phenomena are often observed on the metal foil, and that alters the concentration of the substances contained in the column, thereby spoiling their reaction characteristics.

OBJECT AND SUMMARY OF THE INVENTION

The object of the present invention is to propose apparatus for immunological analysis that mitigates the above-specified drawbacks of the two techniques that presently provide the best performance.

This object is achieved by the apparatus of the invention which, in characteristic manner, is in the form of a kit comprising two distinct elements designed to be assembled together and to co-operate during immunological analysis proper; the first element being an incubation element that includes at least one receptacle suitable for receiving as its contents a mixture made up of a substance to be analyzed and a test substance; and the second element constituting a reaction element including at least one well which is closed by a sealing membrane and which has a bottom on which a reactionally sensitive layer is fixed. In addition, the apparatus of the invention includes, in association with the first and second elements, both means for assembling said elements together, and perforation and injection means which are suitable firstly for perforating the membrane, and then for injecting the contents of the receptacle into the well through said perforated membrane, once the two elements have been assembled together.

Document EP 0 054 087 does indeed describe analysis apparatus which comprises two elements that include means for assembling them together and perforation means, and which are designed to be assembled together during analysis proper. However, the structure of those two elements and their respective functions are totally different from the subject matter of the present invention. In particular, the two elements are not distinct, and the apparatus is not a kit; the first element of document EP 0 054 087 does not include an incubation receptacle; and the second element of document EP 0 054 087 includes an open cavity on which no provision is made for fixing a reactionally sensitive layer; whereas, on the contrary, the well of the second element of the device of the invention is closed by a sealing membrane, and a reactionally sensitive layer is fixed on the bottom thereof.

Thus, during manufacture of the apparatus, the two elements are totally independent. The two elements co-operate for the purpose of immunological analysis only once they have been assembled together. This separation as two distinct elements can present the further advantage of minimizing the volumes of special substances that need to be conserved with care, in particular under determined temperature conditions, since that applies to the second reaction element only, thus leaving the first incubation element free for storage without taking special precautions.

Preferably, the perforation and injection means comprise a tapering tube extending from the bottom of the receptacle of the incubation element and pointing outwards, the inside orifice of said tube having a diameter such that the contents of the receptacle can diffuse therethrough only under drive from a determined amount of centrifugal force. In addition, said tapering tube is disposed so as to perforate the sealing membrane when the two elements are assembled together.

Given the special size of the orifice inside the tube, the contents of the receptacle cannot flow out through the tube during storage, but can be caused to pass therealong, from the receptacle of the incubation element to the well of the reaction element, merely by centrifuging. The narrowest diameter of the tube should lie in the range 0.5 mm to 0.7 mm, for example.

It will be understood that the assembly means associated with the two elements must make it possible to position one of the elements relative to the other in such a manner as to enable the tapering tube to perforate the sealing membrane and penetrate into the well once the assembly operation has been performed.

The assembly means preferably consist:
a) for the incubation element, in fixing tabs which project beneath the bottom of the receptacle far enough to constitute legs that protect the tapering tube; and
b) for the reaction element, in recesses in which said fixing tabs can be snap-fastened.

Thus, by this special disposition, the fixing tabs serve not only to stabilize the incubation element during storage, but also to protect the tapering tubes projecting from the receptacles.

Advantageously, the well contains a substance suitable for keeping the sensitive layer moist. In particular the substance may be a protein solution, a sugar solution, or a gel. This makes it possible to avoid dehydration operations after the reactionally sensitive layer has been fixed on the bottom of the well, thereby guaranteeing better stability of the biologically active substances that have been fixed in this way.

Preferably, the substance suitable for keeping the sensitive layer moist possesses chromotographic properties such that, under the action of centrifugal force, the corpuscular elements diffuse towards the bottom of the well more quickly than do the proteins.

In one embodiment, the reaction element is constituted:
a) by a thin plastics tape in which a plurality of V- or U-bottomed wells are formed;
b) by a support base having a plurality of open-ended recessed portions each serving to receive one well whose bottom is accessible by transparency for examining the results of the analysis; and
c) by a sealing membrane covering all of the wells and fixed to the supporting base in such a manner as to close all of the wells in sealed manner.

In another embodiment, the reaction element no longer includes a preformed tape, but only a supporting base, e.g. made of injection-molded plastic, in which the recessed portions are not open-ended but have bottoms that are accessible by transparency, constituting V-bottom or U-bottom wells.

The support base may be constituted, in particular, by a conventional microtiter plate having 96 wells, organized in 8 rows of 12 wells each.

The invention also provides a method of immunological analysis that implements the above-specified apparatus having receptacles whose bottoms are provided with tapering tubes.

In characteristic manner, the method of the invention comprises the following steps:
a) assembling an incubation element that contains in its receptacle a mixture of substances including the substance to be analyzed and the test substance, and whose bottom is extended externally by a tapering tube whose inside diameter is such as to prevent the mixture from passing therethrough during assembly and incubation, with a reaction element that includes a well closed by a sealing membrane and having a bottom on which there is fixed a reactionally sensitive layer, said assembly being made in such a manner that the tapering tube perforates the sealing membrane and penetrates into the well;
b) incubating said mixture; and
c) centrifuging the two assembled-together elements at a speed sufficient to cause the mixture to pass from the receptacle into the well via the tapering tube.

Preferably, the reactionally sensitive layer is covered in a hydrating substance having chromatographical properties, the method including an additional step of centrifuging at a speed sufficient to obtain differentiated diffusion of the component substances of the mixture through the hydrating substance.

BRIEF DESCRIPTION OF THE DRAWINGS

The present invention will be better understood on reading the following description of a particular embodiment of the immunological analysis apparatus and of its implementation, as illustrated in the accompanying drawings, in which.

MORE DETAILED DESCRIPTION

Figure 1:
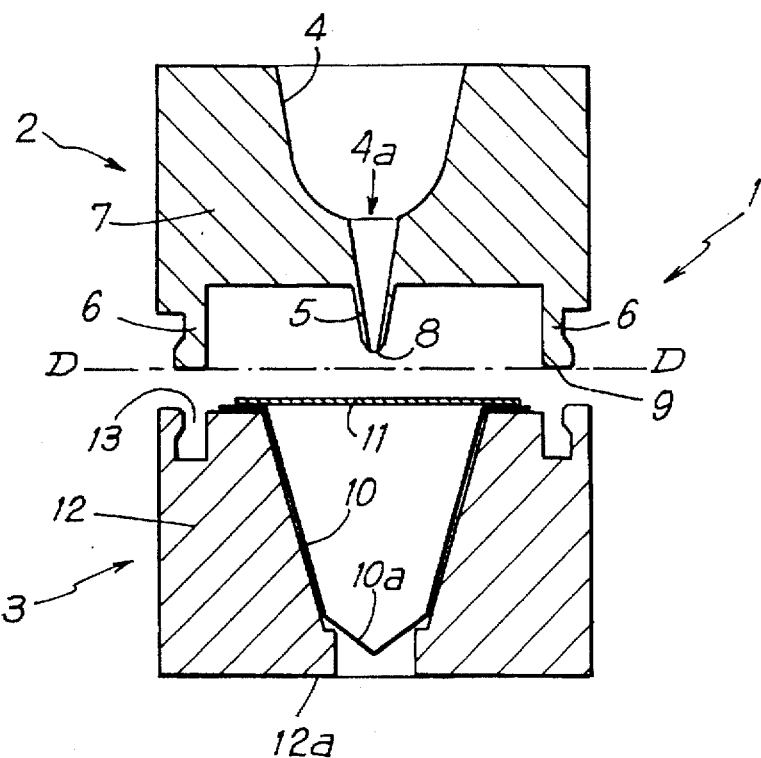
FIG. 1 is a diagrammatic section through two incubation and reaction elements as superposed and prior to assembly.

The immunological analysis kit 1 of the invention comprises two distinct elements 2 and 3 whose manufacturing and storage circuits can be independent, but which are designed to be assembled together and to co-operate during immunological analysis.

The first element 2 referred to as the "incubation" element includes at least one receptacle 4 and generally a plurality thereof. Each receptacle 4 is constituted by a well having a U-shaped bottom, and a capacity of about 100 µl to 200 µl. The bottom 4a of the receptacle is extended by a tapering tube 5 whose inside diameter is about 0.5 mm. The size of this diameter is such as to prevent liquids contained in the receptacle 4 from flowing out under natural gravity alone.

The incubation element also has fixing tabs 6. The tabs 6 extend the body 7 of the incubation element 2 over sufficient height to enable the free end 8 of the tapering tube 5 to remain above the plane DD containing the free ends 9 of said tabs 6. Thus, when the incubation element 2 is stored, it stands on its fixing tabs 6 without any risk of striking the free ends 8 of its tapering tubes 5.

The reaction element 3 includes at least one well 10 and more generally a plurality of wells 10 in the same number as the number of receptacles 4 of the corresponding incubation element 2.

The V- or U-shaped bottom 10a of each well 10 has a reactionally sensitive layer fixed thereon.

Each well 10 is closed in sealed manner by a membrane 11, e.g. a plastic-coated metal foil.

The well 10 is disposed in a substantially conical recess formed in a support 12 and passing right through the support so that the bottom 10a of the well 10 is visible from the bottom face 12a of the support 12, thereby making the results of the immunological analysis accessible by transparency.

The support 12 also includes snap-fastening holes 13 shaped to receive the fixing tabs 6 of the incubation element 2, or else it includes a groove for nesting purposes. The depth of the snap-fastening holes 13 is determined so that once snap-fastening has been performed, the end 8 of each tapering tube 5 lies inside the corresponding well 10.

Since the apparatus is of modular type, as described in document FR 2 655 151, both elements 2 and 3 are made from blocks of plastic, thereby conferring rigidity on the assembly and making it easy to handle, the incubation element 2 being made out of a transparent plastic and the reaction element 3 being made of the same material or else of a colored injection-molded plastic.

In this case, the receptacles 4 constitute integral portions of said block, while the tapering tubes 5 are elements that are added to said block.

The wells 10 of the reaction element 3 are preformed in a thin sheet of plastics material, e.g. a polycarbonate, and each of them has a content of about 100 µl to 250 µl. Each well 10 initially receives a sensitization treatment known as "coating" on its bottom portion corresponding to the bottom 10a. This sensitization treatment is designed to fix a reactionally sensitive layer to the plastic material constituting the bottom 10a of the well 10. Naturally, the layer is made of a material that depends on the type of immunological analysis that is intended. It is constituted, in particular, by antigens or by antibodies.

After the sensitization treatment, a macromolecular liquid or Sephadex type gel is preferably added into the well 10 so as to enable the sensitive layer to be maintained in a moist state.

The preformed plastics sheet is inserted in the plastic block 12.

As described in document FR 2 655 151, the outside surface of said block may receive identification in the form of a bar code or a magnetic track, for the purpose of enabling the apparatus of the invention to be treated automatically.

The apparatus 1 is implemented as follows. The operator inserts a mixture of the substance to be analyzed and of the test substance into the receptacles 4 of the incubation element 2. For example, when screening for antibodies that are irregular in immunohematology, and using apparatus 1 having four wells 10, the receptacles 4 receive 30 µl of serum from the patient and 30 µl of test red blood cells in a 0.2% suspension. In practice, three different kinds of test red blood cells are placed in the first three receptacles, while the fourth receptacle is used as a control.

The wells 10 of the reaction element 3 have previously been sensitized with human antiglobulin antibodies.

Figure 2:
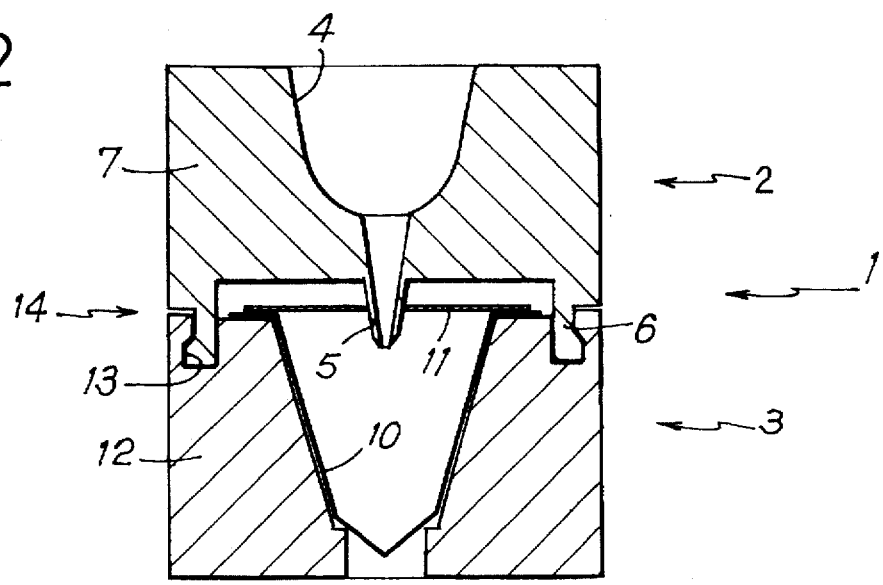
FIG. 2 shows the same elements as in FIG. 1, but after they have been assembled.

The incubation element 2 is placed over the reaction element 3 so as to cause the fixing tabs 6 to penetrate into the holes 13 until said tabs 6 snap-fasten in said holes 13. While this is being done, the tips 8 of the tapering tubes 5 come into contact with the outside surface of the sealing sheet 11 and then progressively perforate it until said tips 8 have all penetrates into the wells 10, as shown in FIG. 2.

The module 14 constituted by both the incubation element 2 and the reaction element 3 as assembled together in this manner is then placed in an incubator, e.g. for a period of 15 minutes at 37° C., or else it is placed in a ventilated cabinet.

After incubation, the assembled module 14 is placed in a centrifuge. The centrifuging speed is initially determined so that the mixture of serum and test-red blood cells passes through the tapering tube 5 under drive from the centrifugal force so as to be injected into the well 10. The acceleration may be 80 g, for example.

When the well 10 also contains a hydrating component, e.g. a Sephadex gel, a higher centrifuging speed is then applied so as to provide centrifugal force capable of driving the test red blood cells so that they come into contact with the V-shaped bottom 10a of the well 10. This speed may be sufficient to apply acceleration of 150 g for a period of 1 minute.

When binding takes place between the test red blood cells and the antiglobulin fixed on the bottom 10a of a well, then uniform distribution over the entire bottom 10a is observed and the reaction is positive.

Otherwise, when no binding is observed, the test red blood cells concentrate in the central portion of the bottom 10a, and the reaction is negative.

On reading the above description, it will be understood that the tapering tube system of the apparatus of the invention makes it possible to transfer the mixture disposed in the incubation element into the reaction well without any risk of cross-contamination and without any risk of losing such fractions of the reagent as might have condensed or splashed during transport, in particular on the underside of the protective foil.

Given that the sealing membrane which serves as the protective foil remains permanently in place, any risk of the foil tearing and then being removed in part only (as can happen using prior art apparatuses) is also avoided.

Figure 3:
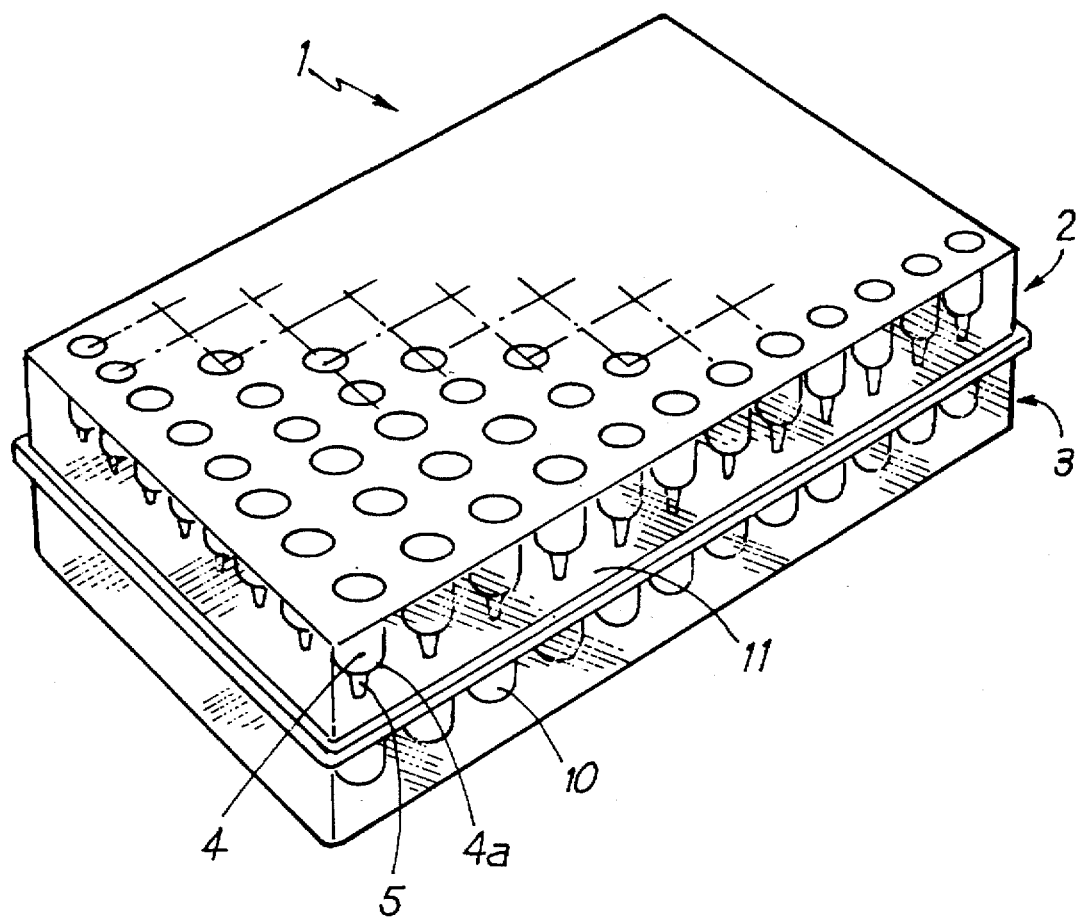
FIG. 3 is a diagrammatic perspective view of a kit of the invention having 96 wells.

The example described relates to modules that have a small number of reaction wells only, e.g. four. Naturally, the modules could have a much larger number of wells, e.g. constituting microtiter type strips or plates, as shown in FIG. 3 where a plate has 96 receptacles and 96 wells disposed in 8 rows of 12 wells each.

Preferably, the sensitization treatment of the bottoms 10a of the wells 10 is based on electrostatic adsorption of proteins onto the plastics material constituting the well.

Also preferably, a polyvalent or IgG reaction antiglobulin is fixed on the bottom of said well rather than establishing a carpet of red blood cells as in the technique proposed by Immucor. Thus, the method of the invention avoids washing, thereby achieving an appreciable saving in time and giving rise to greater stability and reproducibility. Washings can sometimes lead to fixed red blood cells being torn away, and therefore to false-positive reactions due to indicator absorption or to reactions of dubious appearance. In the prior art, the washing stages have constituted stumbling blocks for inexperienced users.

It should be observed that the gel used in the reaction well 10 has a function of hydrating and protecting the sensitive layer on the bottom 10a of the well 10. The gel never contains a reagent, unlike the TAC technique. The purpose of having the gel present or of having other macromolecular liquids present is to avoid implementing dehydration procedures after the bottom 10a has been sensitized, thereby guaranteeing better stability of the biologically active substances.

The gel advantageously comprises 1% bovine albumin to saturate sites that have not been coated. The Sephadex gel may possibly be replaced by a 30% albumin solution or by some other macromolecule that includes a protective and hydrating function.

Chromatography takes place through the gel during centrifuging. That slows down diffusion of free proteins in the reaction medium and allows the red blood cells to descend more quickly.

Unlike the TAC technique, in the present method, red blood cells are never agglutinated so as to enable the reaction of adhesion to the bottom 10a of the well 10 to take place.

The present invention is not limited to the embodiment described above by way of non-exhaustive example. In particular, the assembly means proposed may have numerous different forms providing the main function required of them is performed, i.e. they enable a compact and easily-handled module to be assembled together from the incubation element and the reaction element, thereby making it possible to obtain, by perforation and injection means, the ability to transfer the contents of the incubation receptacle into the reaction well. The assembly means may, in particular, operate by mutual engagement of a male portion and of a female portion disposed respectively on the incubation element and on the reaction element, or vice versa.

I claim:

1. An apparatus for immunological analysis, comprising two independent elements including assembly means to attach the two independent elements in a fluid tight relationship, the first element being an incubation element that includes at least one receptacle having an orifice to accommodate a tapering tube having a tip which is in a fluid relationship with the interior of the receptacle suitable for receiving as its contents a mixture made up of a substance to be analyzed and a test substance, the second element constituting a reaction element including at least one well the upper opening of which is closed by a sealing membrane and which has a bottom and an inside portion on which a reactionally sensitive layer is fixed, wherein the bottom of the receptacle is extended externally by the tapering tube, the inside orifice of which extends from the bottom of the receptacle to the tip of said tube wherein the incubation element being placed over the reaction element, the two elements assembled together in a fluid tight relationship, by the assembly means are positioned relative to each other in such a manner that the tip of the tapering tube of the incubation element perforates the sealing membrane and penetrates into the well of the reaction element wherein the diameter of the inside orifice of the taping tube is such that the mixture contained in the receptacle diffuses from the receptacle of the incubation element into the bottom of the reaction element only under drive from a determined centrifugal force which does not destroy the substance to be analyzed and the test substance.

2. The apparatus according to claim 1, wherein the assembly means consisting of: a) tabs that are attached to and project beneath the receptacle to create legs that protect the tapering tube: and b) the reaction element having a means to mate in a snap-fastening relationship with the fixing tabs of the receptacle such that the receptacle and the reaction element are joined as a single unit.

3. The apparatus according to claim 1, wherein the reaction element comprises:

a) a thin plastics tape in which a plurality of V- or U-bottomed wells are formed;

b) a support base having a plurality of open-ended recessed portions each serving to receive one well whose bottom is accessible by transparency for examining the results of the analysis; and c) a sealing membrane covering all of the wells and fixed to the supporting base in such a manner as to close all of the wells in sealed manner.

4. The apparatus according to claim 1, wherein the well contains a substance suitable for keeping the sensitive layer moist, said substance selected from the group consisting of a protein solution, a sugar solution, or a gel.

5. The apparatus according to claim 4, wherein the substance suitable for keeping the sensitive layer moist possesses chromotographic properties such that, under the action of centrifugal force, the corpuscular elements diffuse towards the bottom of the well more quickly than do the proteins.

6. The apparatus according to claim 1, wherein the reaction element comprises:

a) comprises support base having a plurality of closed-ended hollow recessed portions constituting V- or U-bottomed wells, said bottom being accessible by transparency for examining the results of the analysis; and b) a sealing membrane covering all of the hollow portions and fixed to the supporting base in such a manner as to close all of the wells in sealed manner.

7. The apparatus according to claim 6, wherein the incubation element and the reaction element comprise respectively 96 receptacles and 96 wells, organized as eight rows of twelve each.

8. A method of immunological analysis implementing the apparatus according to claim 1 comprising the following steps:

a) adding the substance to be analyzed to the incubation element wherein said element includes the test substance;

b) assembling the incubation element whose bottom is extended externally by a tapering tube whose inside diameter is such as to prevent the mixture from passing therethrough during assembly and incubation, with a reaction element that includes a well closed by a sealing membrane and having a bottom on which there is fixed a reactionally sensitive layer said assembly being made in such a manner there the tapering tube perforates the sealing membrane and penetrates into the well;

c) incubating said mixture; and d) centrifuging the two assembled-together elements at a speed sufficient to cause the mixture to pass from the receptacle into the well via the tapering tube.

9. The method according to claim 8, wherein the reactionally sensitive layer is covered in a hydrating substance having chromatographcial properties, the method including an additional step of centrifuging at a speed sufficient to obtain differentiated diffusion of the component substances of the mixture through the hydrating substance.

* * * * *